United States Patent [19]

Smith

[11] Patent Number: 4,493,709
[45] Date of Patent: Jan. 15, 1985

[54] METERING DEVICE FOR INTRAVENOUS FLUIDS

[75] Inventor: Gordon E. Smith, Carrollton, Tex.

[73] Assignee: Quest Medical, Inc., Carrollton, Tex.

[21] Appl. No.: 342,100

[22] Filed: Jan. 25, 1982

[51] Int. Cl.³ .............................................. A61M 5/00
[52] U.S. Cl. .................................... 604/246; 604/250; 225/450
[58] Field of Search ................ 604/33, 186, 237, 246, 604/250; 222/207, 212, 447, 450, 639

[56] References Cited

U.S. PATENT DOCUMENTS

| 16,284 | 12/1856 | Mason | 222/249 |
|---|---|---|---|
| 4,121,584 | 10/1978 | Turner et al. | 604/246 |
| 4,191,184 | 3/1980 | Carlisle . | |
| 4,204,538 | 5/1980 | Cannon | 604/246 |
| 4,205,238 | 5/1980 | Shim | 604/246 X |
| 4,207,871 | 6/1980 | Jenkins | 604/246 X |
| 4,230,244 | 10/1980 | Zissimopoulos | 604/246 X |
| 4,261,356 | 4/1981 | Turner et al. | 222/450 X |
| 4,262,668 | 4/1981 | Schmidt | 222/450 X |
| 4,262,824 | 4/1981 | Hrynewycz | 604/246 X |
| 4,304,260 | 12/1981 | Turner et al. | 222/450 X |

FOREIGN PATENT DOCUMENTS

| 1077943 | 11/1954 | France . |
|---|---|---|
| 1115231 | 5/1968 | United Kingdom . |
| 1025728 | 8/1966 | U.S.S.R. . |

Primary Examiner—Stephen C. Pellegrino
Attorney, Agent, or Firm—Isaksen, Lathrop, Esch, Hart & Clark

[57] ABSTRACT

A metering device is disclosed which includes a metering chamber (14) divided into two compartments (22, 24) by a pressure transmitting member in the form of a flexible diaphragm (20). Fluid flow is alternately allowed into each of the two compartments (22, 24) with each compartment filling to the volume of the metering chamber (14) when full so that periodic pulses of intravenous fluid of that precise volume are sent to the patient. The volume of the metering chamber (14) is selected to match a standard intravenous set drop size, for example one-tenth, one-fifteenth, one-twentieth, or one-sixtieth milliliter.

8 Claims, 4 Drawing Figures

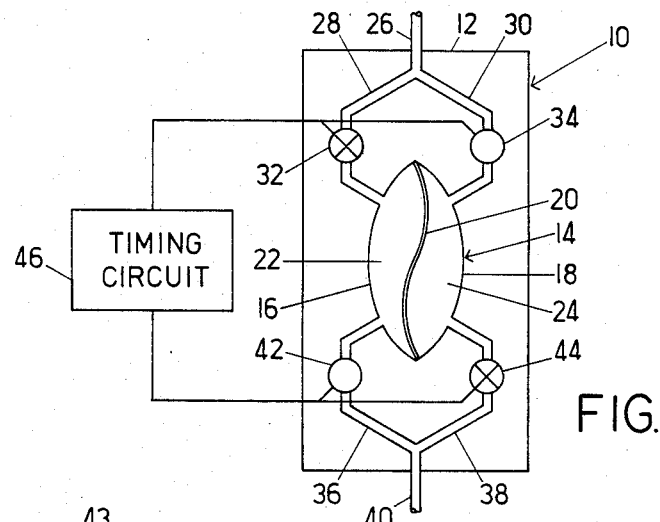
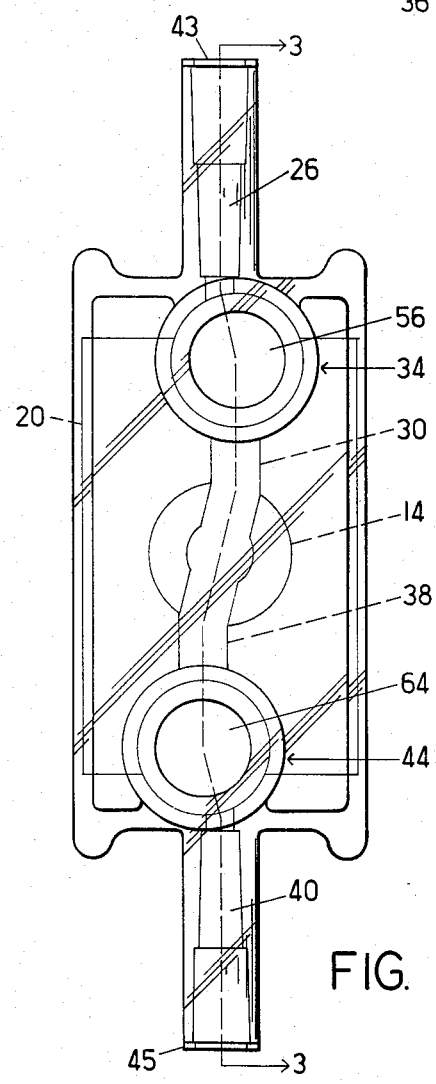
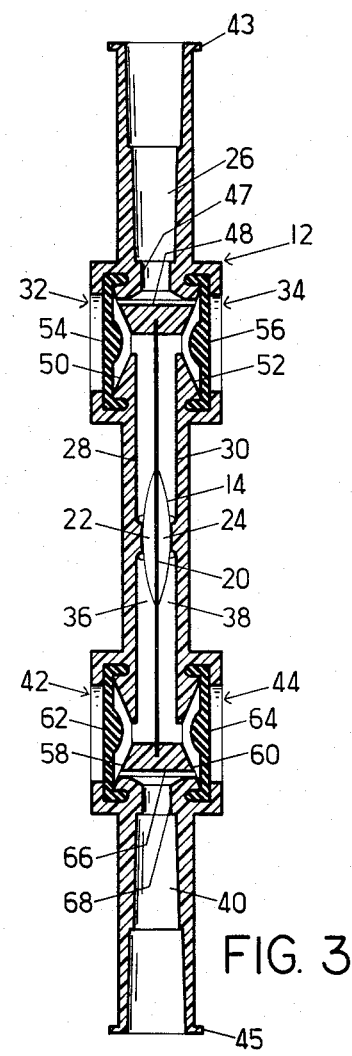

METERING DEVICE FOR INTRAVENOUS FLUIDS

FIELD OF THE INVENTION

The present invention relates to metering devices for the introduction of intravenous fluids into a patient and, in particular, to such devices which are passive, in the sense that they do not actively pump fluid, yet which accurately meter and control the fluid flow into the patient.

DESCRIPTION OF THE PRIOR ART

Generally at the present time in hospital environments, the flow of intravenous fluid from an intravenous source, such as an IV bottle or bag, is generally controlled by an adjustable pinch clamp connected over the tubing connecting the IV source to the patient. Typically, a drip chamber is provided along the fluid path of the intravenous fluid, and the rate of fluid flow into the patient is controlled by adjusting the pinch clamp to provide a selected number of drops per interval of time as counted by the nurse or technician in the drip chamber. It is often considered to be a convention in the medical field that, depending on the size of the IV system, each of such drops has an approximately standard volume, typically 0.1 milliliters or (0.1 cc), so that the average rate of fluid flow into the patient is normally determined by dividing the number of drops per minute by the volume of the drop to get a value for the overall flow rate expressed in milliliters per minute. Other standard drop volumes are one fifteenth, one twentieth, and one sixtieth of a milliliter, with the one-sixtieth milliliter drop size being used in pediatric equipment.

Various prior art devices have been proposed to monitor and control the flow of intravenous fluids into a patient. A device is disclosed in a pair of patents, U.S. Pat. Nos. 4,204,538 and 4,207,871, which is designed to measure and control the flow of intravenous fluid into a patient. In the device disclosed in those two patents, the rate of fluid flow is monitored, that is to say measured, through use of a chamber which is divided into two compartments by a diaphragm with the movement of the diaphragm being monitored by a transducer. By appropriate electronic monitoring of the position of the transducer, the apparatus described in these patents operates a series of valves to alternately allow fluid flow into each of the two chambers formed in opposite sides of the diaphragm. The chamber of that device is used to measure the rate of fluid flow while a pinch clamp is used to actually control the rate of flow of fluid flow into the patient. Adjustments of the pinch clamp are made in that apparatus through appropriate electronic analysis of the transducer. The fluid flow is constant through the device into the patient.

There are also examples known in the prior art of devices which fill and then empty chambers of known volume to meter fluids for one purpose or another. In U.S. Pat. No. 4,121,584, an apparatus for controlling the dispensing of fluid is disclosed which includes a metering chamber of a predetermined volumetric size which is alternatively filled and then emptied by appropriate controlling apparatus to introduce specific desired increments of fluid into a patient. U.S. Pat. No. 16,284 discloses a meter for metering out large volumes of fluid by alternately filling two chambers formed on opposite sides of a membrane. A device is disclosed in French Pat. No. 2,346,238 which includes a reservoir having two hemispheres divided by a flexible membrane into two compartments. In that device, one compartment is intended to be alternately filled and then emptied by fluids which may be introduced into a patient while the other compartment receives a different fluid. U.S.S.R. patent certificate No. 1025728/28-13 discloses a device for the injection of brine into a pork ham which includes a chamber divided into two compartments by a diaphragm. Alternately, the two compartments are filled and emptied from a brine source with the fluid emptying from the compartment into a suitable ham. A valving mechanism is described for the device disclosed in the U.S.S.R. Certificate to connect the fluid alternatively into compartments on opposite sides of the diaphragm.

SUMMARY OF THE INVENTION

The present invention is summarized in that a metering device for monitoring and controlling the flow of intravenous fluid includes: a metering chamber having a fixed volume; a pressure transmitting device dividing the metering chambers into first and second compartments; respective inlet and outlet tubes connected to each of the first and second compartments in the metering chamber; valve means connected on each of the respective inlet and outlet tubes connected to each of the first and second compartments in the metering chamber; main inlet and outlet tubes, each of which connects to the respective inlet tubes or outlet tubes connected to the two compartments in the metering chamber; and a timing circuit to control the operation of the valve means so as to repetitively and alternatively allow fluid to flow into and out from each of the two compartments formed in the metering chamber; the total volume of the metering chamber being equal to a standard drop volume of no greater than 0.1 milliliters and each of the compartments in the metering chamber being equal to the volume of the metering chamber when that compartment is filled with fluid, such that the metering device causes an amount of fluid of precisely the standard drop volume to be introduced into the main outlet tube upon each switching of the timing circuit.

It is an object of the present invention to provide a metering device for intravenous fluids which is capable of providing pulsed drops of fluid which are equal in volume to the volume of a standard drop volume as currently measured in practice in medical environments.

It is another object of the present invention to provide a metering device for intravenous fluids which is designed to introduce pulses of fluid flow, rather than continuous fluid flow, into the patient so as to prevent obstruction or occlusion of an intravenous needle introduced into a patient's vein.

It is another object of the present invention to provide such a metering device which is extremely accurate and volumetric in the metering of intravenous fluid and which is capable of operation with no additional pressure requirement other than the head pressure of the intravenous source of fluid.

Other objects, advantages and features of the present invention will become apparent from the following specification when taken in conjunction with the accompanying drawings.

BRIEF DESCRIPTION OF THE DRAWINGS

FIG. 1 is a schematic illustration of the metering device.

FIG. 2 is an elevation view of the cassette.

FIG. 3 is a side cross-sectional view taken along line 3—3 of FIG. 2.

Illustrated in schematic fashion in FIG. 1, and generally designated at 10, is a metering device for intravenous fluids constructed in accordance with the present invention. As illustrated in FIG. 1, most of the main components of the metering device 10 are concentrated around or within a cassette 12. The cassette 12 has formed within it a metering chamber 14 of fixed geometric shape and volume. The metering chamber 14 is of a lenticular, or lens-like, shape and is constructed to have a volume equal to a standard IV drop size, preferably 0.1 milliliters, or 0.1 cc. The metering chamber 14 is defined between a pair of concave side walls 16 and 18 which are shaped and sized to give the metering chamber 14 the preselected desired size. A pressure transmitting membrane 20 divides the metering chamber 14 into a pair of compartments 22 and 24, formed on opposite sides of the membrane 20, between the membrane 20 and the respective chamber walls 16 and 18. A main inlet tube 25 is connected to the cassette 12. Inside the cassette 12, the main inlet tube 26 branches into a pair of inlet tubes 28 and 30 which open respectively into the compartments 22 and 24. Each of the inlet tubes 28 and 30 has provided in it and is controlled by one of a pair of respective inlet valves 32 and 34. In the illustration of FIG. 1, the inlet valve 32 is shown as closed, while the inlet valve 34 is illustrated as open. Also opening into each of the respective compartments 22 and 24 through the chamber walls 16 and 18 is one of a pair of outlet tubes 36 and 38. The outlet tubes 36 and 38 join inside the cassette 12 to form a common main outlet tube 40 exiting from the cassette 12. The outlet tubes 36 and 38 are respectively interrupted and controlled by outlet valves 42 and 44, with the outlet valve 44 being shown closed in FIG. 1 and the outlet valve 42 being shown as open. All of the valves 32, 34, 42 and 44 within the cassette 12 are operably connected to a timing circuit 46 which controls the opening and closing of the valves. The timing circuit 46 may be any mechanical or electrical device capable of providing a mechanical or electrical operation of the valves 32, 43, 42, and 44 on a selectable time period basis, but is preferably a solid-state digital circuit which has a selectable time frequency output capable of operating the valves 32, 34, 42, and 44. Such solid-state timing circuits are not described in greater detail here.

Figure 4:
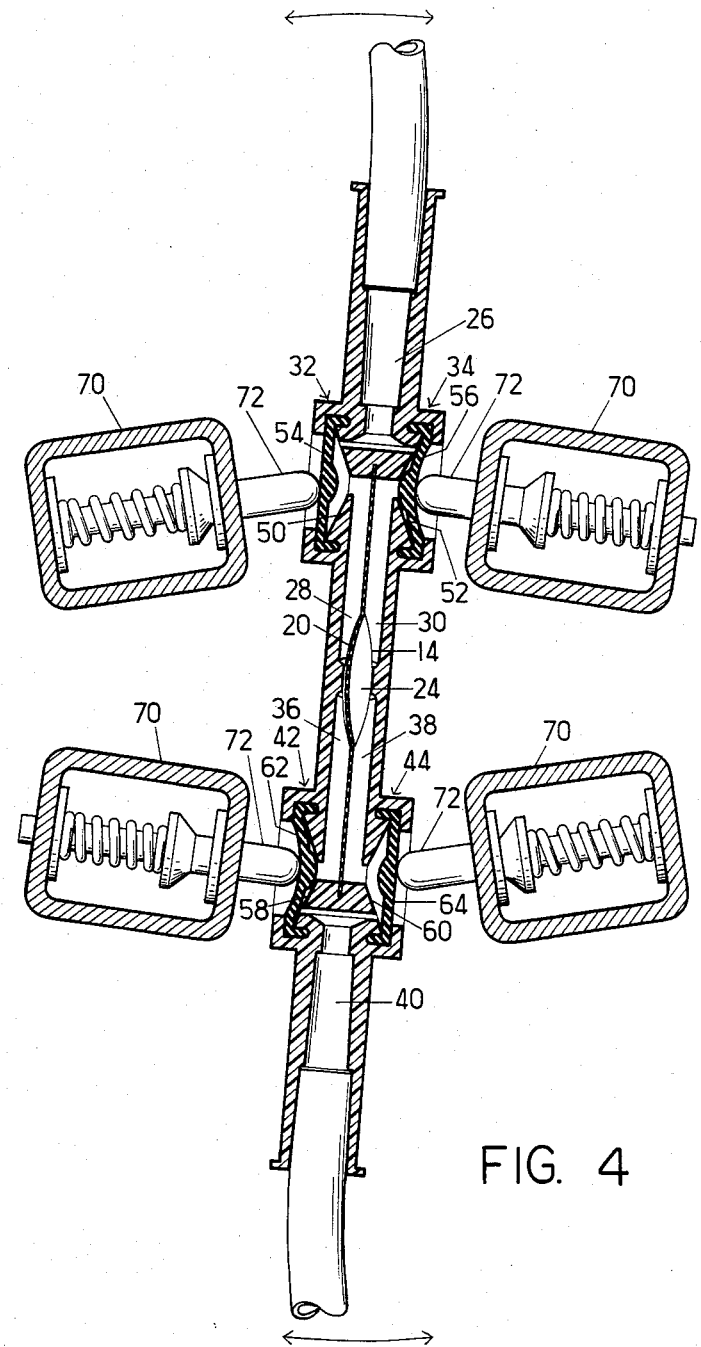
FIG. 4 is a sectional view of the cassette in a metering device.

In its operation, the metering device of FIG. 1 functions to both monitor and control the flow of intravenous fluids from an intravenous source into a patient. The metering device 10 is utilized by connecting an intravenous source of fluid, such as a conventional IV bag or bottle, to the main inlet tube 26 into the cassette 12. The fluid in the source of intravenous fluid should have a head pressure in excess of the blood pressure of the patient. The head pressure is typically created by elevating the IV source above the patient, but can also be created by pressurizing the IV source with mechanical pressure or other means. The main outlet tube 40 from the cassette 12 is then connected through suitable tubing to an intravenous catheter inserted into the arm of the patient.

Operation of the metering device 10 of FIG. 1 is controlled by the timing circuit 46 which acts to alternatively and repetitively close and open pairs of the inlet and outlet valves 32, 34, 42 and 44. The inlet and outlet valves are oppositely paired in their operation, that is to say, the inlet valve 34 and the outlet valve 42 are always simultaneously either opened or closed, while the inlet valve 32 and the outlet valve 44 are also simultaneously either opened or closed. In FIG. 1, the valves 34 and 42 are shown as open, while the valves 32 and 44 are shown as closed. With the inlet valve 32 and the outlet valve 44 closed, fluid flows from the IV source through the main inlet tube 26, through the inlet tube 30, through the open inlet valve 34, and then into the compartment 24 on the right side of the membrane 20 dividing the metering chamber 14. The fluid flowing into the right side of the metering chamber 14 is under pressure from the head pressure of the source of IV fluid. That pressure causes the membrane 20 to be pushed to the left as the membrane 20 transmits that fluid pressure to any fluid present in the compartment 22 on the left side of the membrane 20. The fluid in the compartment 22 is forced out of that compartment through the outlet tube 36, through the open outlet valve 42, into the main outlet tube 40 and into the patient. The fluid entering the patient is thus driven only by the head pressure of the intravenous fluid source. After the compartment 24 is entirely filled with intravenous fluid, i.e. the membrane 20 is pressed against the wall 16 of the metering chamber 14, fluid flow ceases. Since there is no more fluid inside of the compartment 22, no more fluid exits through the outlet tube 36. At this time, the compartment 24 is entirely filled and the compartment 24 entirely fills the volume of the metering chamber 14. Fluid flow remains ceased until the timing circuit 46 switches the state of the valves 32, 34, 42 and 44. When the timing circuit 46 does switch the operation of the valves, the inlet valve 34 and the outlet valve 42 are closed, and the inlet valve 32 and the outlet valve 44 are opened. In that configuration, fluid flow is allowed from the main inlet tube 26, through the inlet tube 28, and the inlet valve 32, into the compartment 22 on the left side of the membrane 20. This flow, in turn, causes the membrane 20 to be pushed to the right, thereby transmitting the pressure from the source of IV fluid to the fluid in the compartment 24 on the right side of the membrane 20. The fluid in the compartment 24 is forced out of the outlet tube 38, through the valve 44, and the main outlet tube 40 and then into the patient. Again, fluid is forced out of the compartment 24 until the compartment 22 is entirely filled and then the fluid flow ceases. Fluid flow again remains ceased until the timing circuit 46 again alternates the opening and closing of the valves.

As stated and as can be readily seen from the schematic view of FIG. 1 that each of the compartments 22 and 24, when filled, occupies a volume equal to the entire volume of the metering chamber 14. Thus, if the metering chamber 14 is constructed to be of a preselected volume equal to the volume of a standard intravenous set drop size, such as a volume of 0.1 milliliters, the volume of each of the compartments 22 and 24 when filled will be precisely equal to each other and equal in volume to 0.1 milliliters. Since following each switching of the actuation of the valves 32, 34, 42, and 44 by the timing circuit 46, one compartment is emptied of fluid while the other compartment is entirely filled with fluid, one pulse of fluid equal in volume to 0.1 milliliters is transmitted through the main outlet tube 40 for each time period set by the timing circuit 46. Thus, the metering device 10 of FIG. 1 functions to precisely output one pulse equal in volume to 0.1 milliliters, for each actuation of the timing circuit 46. The volume of this pulse of fluid which is emitted from the metering device 10 remains constant as long as the timing circuit 46 is set for a time period sufficiently long to allow the respective compartment 22 or 24 being filled to completely fill with fluid before the operation of the valves is reversed. If that condition is met, the volume of the pulse of fluid passing through the outlet tube 40 between each actuation of the valves will be precisely 0.1 milliliter.

Shown in FIGS. 2 through 4 are the construction details of an actual metering device constructed in accordance with the present invention and operation in accordance with the schematic illustration of FIG. 1. Shown in FIGS. 2 and 3 is a cassette 12 constructed as a unitary construction of molded themoplastic material. The cassette 12 has at its upper end a main inlet tube 26 and at its lower end a main outlet tube 40. The main inlet tube 26 and the main outlet tube 40 are provided at their ends with respective luer lock connectors 43 and 45 which are designed to allow a secure luer lock attachment between the cassette 12 and other portions of an intravenous feeding system incorporating therein the cassette 12 of the metering device 10 of the present invention. Fluid passing through the main inlet tube 26 passes through a narrowed opening 47 into a transverse channel 48. The transverse channel 48 extends in the direction transverse to an axis drawn from the main inlet tube 26 to the main outlet tube 40, and the transverse channel extends between the inlet valves 32 and 34. The inlet valves 32 and 34 are each formed from valve chambers 50 and 52 which are formed as outwardly extending open apertures in the body of the cassette 12. Each of the valve chambers 50 and 52 is closed by a respective one of valve members 54 and 56, which are resiliently flexible circular disks, formed of silicone elastomer or similar elastic materials, having a thickened valve seat portion formed in the center thereof. Each of the valve chambers 50 and 52 opens into a respective one of inlet tubes 28 and 30 each of which extends from the respective valve chamber 50 and 52 to open into the metering chamber 14 formed in the center of the cassette 12. The metering chamber 14 is formed as a lenticular hollow in the center of the cassette 12 and is divided into the compartments 22 and 24 by a silicone membrane 20 integrally molded inside of the cassette 12. The membrane 20 is mounted along the length of the longitudinal centerline of the cassette 12 and also serves as a dividing partition between the inlet tubes 28 and 30. The inlet tubes 28 and 30 are relatively narrow, as can be seen by referring to the external view shown in FIG. 2, while the metering chamber 14 is relatively wide and the elasticity of the diaphragm 20 is selected so that it undergoes significant deformation only in the area of the metering chamber 14. A pair of outlet tubes 36 and 38 connect the metering chamber 14 respectively to each of a pair of valves 42 and 44. Each of the valves 42 and 44 includes a respective valve chamber 58 and 60 similar in shape and arrangement to the valve chambers 50 and 52. Each of the valve chambers 58 and 60 is closed by a one of respective valve members 62 and 64 which are similar in construction and appearance to the valve members 54 and 56. A main outlet tube 40 connects through a narrowed opening 66 to a transverse channel connected to the valve chambers 58 and 60.

Shown in FIG. 4 is an installation in which the cassette 12 illustrated in FIGS. 2 and 3 is used in operation in a metering device. The cassette 12 is placed in a mounting bracket (not shown) which is mounted on a motive device capable of oscillatory motion (also not shown). The oscillating motion is provided by a bi-directional rotational motive device, such as a rotational motor with a cam driven oscillating mechanism, a rotational solenoid, or any other oscillating mechanical motive device. The oscillating mechanical device is operated by the timing circuit 46 as illustrated in FIG. 1. The oscillating motive device causes the cassette 12 itself to oscillate backwards and forwards through a small arc about an axis centered in the metering chamber 14. The oscillation of the cassette 12 in FIG. 4 is illustrated by the curved motion lines at the top and bottom of the cassette illutrated in FIG. 4. Four fixed valve operators 70 are provided externally of the cassette 12. The valve operators are fixed in position in the positions shown in FIG. 4. Each of the valve operators 70 includes a spring-loaded plunger 72 oriented in a direction so as to extend into one of the valve chambers 54, 56, 58 or 60. As can be seen in FIG. 4, if the cassette 12 is moved in a clockwise direction in its oscillatory motion, the plunger 72 of a one of the valve operators 70 causes the valve member 56 to be depressed to close the valve 34. At the same time as another of the plungers 72 is forced against the valve member 58 to close the valve 42. With the valves 34 and 42 closed, fluid can flow through the inlet tube 28 into the chamber 22 on the left side of the membrane 20 while fluid is forced out of the compartment 24 through the outlet valve 44. When the timing circuit indicates that the operation of the valves is to be switched, the oscillating mechanism causes the cassette 12 to be rotated counter-clockwise so that the pair of plungers 72 associated with the valves 32 and 44 causes those two valves to be closed while at the same time the valves 34 and 42 are opened. This switching of the valve operation causes fluid to flow into the compartment 24 from the source of intravenous fluid while the compartment 22 is emptied outward into the patient. Thus, it can be seen that the operation of the cassette 12 of FIGS. 2-4 operates in a fashion exactly as described with reference to the schematic view of FIG. 1.

The metering device for intravenous fluids as disclosed in FIGS. 1 through 4 is inherently accurate and volumetric in character. The apparatus is completely volumetric in character in that for each switching of the timing circuit 46, one pulse of fluid equal in volume to the metering chamber 14 is forced from the device into the patient. Thus, by careful construction of the cassette 12 so that the metering chamber 14 is of an accurately preselected volume, the volume of each pulse of fluid which is introduced into the patient can be accurately controlled. Since these metered amounts of fluid are precisely accurate in volume and since the timing of the switching of the timing circuit 46 can be accurately controlled by well-known electronic devices, the rate of fluid flow through the metering device can be accurately controlled. The overall volume of flow can thus be determined over any time period merely by multiplying the number of operations of the timing circuit times the volume of the metering chamber 14.

Fluid exits from the metering device 10 of FIGS. 1 through 4 in a pulsed fashion, i.e. one pulse of short duration for each operation of the timing circuit 46. There are advantages in the use of this device for metering the flow of intravenous fluids into a patient which result from this pulsed operation. Because the fluid comes out in relatively quick pulses, rather than a slow continuous stream, as in conventional equipment, the flow of fluid out of the catheter into the patient's veins is a series of relatively fast, powerful fluid pulses rather than a continuous low pressure stream. These relatively fast fluid pulses tend to lessen the buildup of fibrin over the end of the catheter inserted into the patient by tending to carry such fibrin fibers away in the fluid pulse exiting from the catheter. Because of the rapidity of these pulses, the IV catheter is less likely to be clogged by fibrin buildup than in an installtion using a slow, continuous flow.

One of the primary advantages of the apparatus 10 of FIGS. 1 through 4 is that the size of the chamber can be constructed so as to correspond to the present standard in practice in drop size measured in the field. For example, it is prefered that the volume of the metering chamber 14 in the cassette 12 be selected so as to correspond to a volume of 0.1 milliliters. It is currently standard practice in hospitals to set the rate of fluid flow of intravenous fluid into a patient using a drip chamber in which drops are counted. In that practice with most equipment it is generally considered that 10 drops constitute 1 milliliter of fluid flow. Other widely used equipment has drop sizes of one fifteenth, one twentieth and one sixtieth of a milliliter and the volume of the metering chamber 14 can also be selected to match one of these volumes. By providing that a similar amount exits from the metering device 10 during each of its operations, and by providing that the cassette 12 oscillates in a fashion which can be readily viewed, the hospital staff utilizing this equipment can gain a ready appreciation of the amount of fluid being introduced into a patient since the rate of oscillation of the cassette 12 corresponds exactly to the rate of drop flow which they have historically been required to count in setting up intravenous intallations. Thus, the apparatus of the present invention is particularly well adapted to being utilized in present hospital environments with a minimum of retraining of staff or customization to new techniques. Furthermore, since the total volume of fluid metered by the device equals the volume of the metering chamber 14 times the number of operations of the timing circuit 46, if the volume of the metering chamber 14 is 0.1 milliliter, a simple division of the rate of switching of the timing circuit 46 by 10 gives the total flow rate in milliliters. Obviously, if the volume of the metering chamber 14 is selected instead to match another of the standard flow rates, division in this calculation would change.

Other objects, advantages and features of the present invention will become apparent from the following specification when taken in conjunction with the accompanying claims.

I claim:

1. A metering device for monitoring and controlling the flow of intravenous fluid at a preselected overall volumetric flow rate comprising:

a metering chamber (14) having a fixed accurately preselected volume equal to a standard drop size no greater than 0.1 milliliters;

a pressure transmitting member (20) dividing the metering chamber (14) into first and second compartments (22, 24);

respective inlet and outlet tubes (28, 30, 36, 38) connected to each of the first and second compartments (22, 24) in the metering chamber (14);

valve means (32, 34, 42, 44) connected to each of the respective inlet and outlet tubes (28, 30, 36, 38) connected to each of the first and second compartments (22, 24) in the metering chamber (14);

main inlet (26) and outlet (40) tubes, each of which connects to the respective inlet tubes (28, 30) or outlet tubes (36, 38) connected to the two compartments (22, 24) in the metering chamber (14) the main outlet tube (40) being free from downstream rate-control occlusions; and timing and valve operator means for controlling the operation of the valve means (32, 34, 42, 44) so as to repetitively and alternatively allow fluid flow into and out of each of the two compartments (22, 24) formed in the metering chamber (14) for a time period sufficiently long to allow the compartments to completely fill and empty alternatively, the volume of each of the compartments (22, 24) being equal in volume to the volume of the metering chamber (14) when that compartment is filled so that a pulse of fluid precisely equal to the standard drop size in volume is introduced into the main outlet tube (40) and into the patient upon each switching of the valve means (32, 34, 42, 44) by the timing and valve operator means; the timing and valve operator means constructed so that the time period between valve means operations is equal to the quotient of the metering chamber volume divided by the preselected overall volumetric flow rate, the time period thus being independent both of the instantaneous flow rate and of the positioning of the pressure transmitting member.

2. A metering device as claimed in claim 1 wherein the pressure transmitting member (20) is a flexible elastic diaphragm stretched across the metering chamber (14) so as to divide it into two compartments (22, 24).

3. A metering device as claimed in claim 2 wherein the diaphragm (20) is formed of a silicone elastomer.

4. A metering device as claimed in claim 1 wherein the metering chamber (14) is constructed as a hollow cavity formed in the center of a cassette (12).

5. A metering device as claimed in claim 4 wherein the cassette (12) also includes therein the inlet and outlet tubes (28, 30, 36, 38), the main inlet and outlet tubes (26, 40), and the valve means (32, 34, 42, 44).

6. A metering device as claimed in claim 1 wherein the volume of the metering chamber (14) is equal to 0.1 milliliters.

7. A volumetric metering device for controlling the gravity flow of intravenous fluid in digital pulses at a preselected overall volumetric flow rate through a fluid path extending from a fluid supply to a patient comprising:

(a) a metering chamber having an accurately preselected volume no greater than about 0.1 milliliter, said chamber divided into first and second compartments by a pressure transmitting member, said first and second compartments each having valved inlet and outlet means, and the outlet means being free from downstream rate-control occlusions;

(b) control means for repeatedly driving the apparatus into four conditions sequentially as follows:

(i) inlet to first compartment and outlet from second compartment open; outlet from first compartment and inlet from second compartment closed; thus causing fluid to flow from the supply through the inlet to the first compartment to fill the first compartment, causing movement of the pressure transmitting member to empty the second compartment delivering a volume of fluid equal to the size of the metering chamber into the path to the patient;

(ii) fluid flow stopped following filling of first compartment by continued maintenance in the closed position of at least one of first compartment outlet and second compartment inlet, thus preventing movement of the pressure transmitting member and fluid flow;

(iii) inlet to second compartment and outlet from first compartment open; inlet to first compartment and outlet from second compartment closed; thus causing fluid to flow from the supply through the inlet to the second compartment to fill the second compartment, causing movement of the pressure transmitting movement to empty the first compartment delivering a volume of equal to the size of the metering chamber into the path to the patient;

(iv) fluid flow stopped following filling of second compartment by continued maintenance in the closed position of at least one of second compartment outlet and first compartment inlet, thus preventing movement of the pressure transmitting member and fluid flow; and (c) timing means forming a part of the control means for selecting an overall volumetric rate of fluid flow to be delivered to the patient, completely independently of the instantaneous flow rate and the positioning of the pressure transmitting member, comprising means for setting a constant time lapse between the switching of valves for commencement of condition (i) and condition (iii) equal to the quotient of the chamber volume divided by the overall volumetric flow rate.

8. A method of supplying fluid on a volume controlled basis in digital pulses to a patient intravenously employing a supply of fluid elevated above the patient and connected to the patient by a fluid path free of downstream rate-control occlusions which contains a metering chamber of predetermined volume no greater than about 0.1 milliliter separated into first and second compartments by flexible membrane, the chamber having valve means controlling upstream entrance to, and downstream exit from, each of said compartments comprising:

(a) selecting an overall volumetric flow rate, but not an instantaneous flow rate, at which fluid is to be delivered to the patient over time;

(b) causing fluid to flow into the first compartment and from the second compartment by setting the valve means to a first state opening only the first compartment entrance to fluid from the upstream supply and opening only the exit of the second compartment to passage of fluid downstream toward the patient, whereby fluid from the supply fills the first compartment and forces the flexible membrane to move across the chamber delivering a volume of fluid equal to the size of the chamber from the second compartment toward the patient;

(c) stopping all flow of fluid after filling of the first compartment by maintaining in the closed position at least one of the outlet from the first compartment and the inlet to the second compartment, until a predetermined time period has elapsed from the setting of the valve means into the first state the time period being equal to the quotient of the volume of the metering chamber divided by the overall volumetric rate of flow selected;

(d) upon the lapse of such predetermined period of time from the setting of the valve means into the first state switching the valve means to a second state opening only the second compartment entrance to fluid from the upstream supply, and opening only the exit of the first compartment to passage of fluid downstream to the patient, whereby fluid from the supply fills the second compartment and forces the flexible membrane to move across the chamber delivering a volume of fluid equal to the size of the chamber from the first compartment toward the patient;

(e) stopping all flow of fluid after filling of the second compartment by maintaining in the closed position at least one of the outlet of the second compartment and the inlet of the first compartment until the identical predetermined period has elapsed from the setting of the valves into their second state;

(f) upon the lapse of such identical time period from the setting of the valve means into the second state, returning the valve means to the first state, and then continuing steps (b) through (f) until the overall volume of fluid desired for the patient has been delivered.

* * * * *